US006823212B2

(12) United States Patent
Pinyayev

(10) Patent No.: US 6,823,212 B2
(45) Date of Patent: Nov. 23, 2004

(54) METHOD AND APPARATUS FOR MEASURING PROPERTIES OF A TARGET SURFACE

(75) Inventor: Aleksey Mikhailovich Pinyayev, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 529 days.

(21) Appl. No.: 09/879,706

(22) Filed: Jun. 13, 2001

(65) Prior Publication Data

US 2003/0004431 A1 Jan. 2, 2003

(51) Int. Cl.[7] ................................................ A61B 5/05
(52) U.S. Cl. ..................... 600/547; 600/306; 600/382; 600/293
(58) Field of Search ................................ 600/547, 383, 600/384, 386, 393, 587, 306, 307, 345, 357, 382

(56) References Cited

U.S. PATENT DOCUMENTS

| | | | |
|---|---|---|---|
| 3,665,302 A | 5/1972 | Lees et al. | |
| 4,164,214 A | 8/1979 | Stark et al. | |
| 4,494,554 A | 1/1985 | Van Dyke et al. | |
| 4,537,573 A | 8/1985 | Sunada | |
| 4,758,778 A | 7/1988 | Kristinsson | |
| 5,053,703 A | 10/1991 | Fischer | |
| 5,239,258 A | 8/1993 | Kauffman | |
| 5,353,802 A | 10/1994 | Ollmar | |
| 5,738,107 A | 4/1998 | Martinsen et al. | |
| 5,938,593 A | 8/1999 | Ouellette | |
| 5,961,471 A | 10/1999 | Nickson | |
| 5,964,703 A * | 10/1999 | Goodman et al. | 600/547 |
| 6,041,253 A | 3/2000 | Kost et al. | |
| 6,085,115 A | 7/2000 | Weaver et al. | |
| 6,400,983 B1 * | 6/2002 | Cha | 600/547 |
| 6,487,449 B1 * | 11/2002 | Kaiser et al. | 600/547 |
| 6,501,984 B1 * | 12/2002 | Church et al. | 600/547 |
| 6,516,218 B1 * | 2/2003 | Cheng et al. | 600/547 |
| 6,564,079 B1 * | 5/2003 | Cory et al. | 600/393 |
| 6,654,634 B1 * | 11/2003 | Prass | 600/547 |

FOREIGN PATENT DOCUMENTS

| | | |
|---|---|---|
| GB | 2298923 A | 9/1996 |
| WO | WO 98/22182 | 5/1998 |
| WO | WO01301 A1 | 1/2000 |

OTHER PUBLICATIONS

SERUP and JEMEC, Handbook of Non-invasive Methods and the Skin, Chapt. 9, CRC Press, 1995.

* cited by examiner

Primary Examiner—Fadi H. Dahbour
(74) Attorney, Agent, or Firm—Larry L. Huston; Leonard W. Lewis; Steven W. Miller

(57) ABSTRACT

A method for measuring the barrier properties of naturally occurring tissue, such as the skin. The method comprises the steps of providing a probe having a pair of spaced apart electrodes in electrical communication with each other, a voltage generator capable of supplying an increasing voltage between said electrodes, and a voltage meter capable of indicating the voltage between said electrodes. The electrodes are placed in contact with the target surface. An increasing voltage from is supplied from the voltage generator to the electrodes until current between said electrodes reaches a predetermined value. The voltage, which occurs when the current reaches the predetermined value, is noted. In another embodiment the invention comprises a device for measuring the barrier properties of the skin. The device comprises a probe. The probe has a pair of spaced apart electrodes in electrical communication with each other. The electrodes are noninvasively contactable with the skin of a subject, or other target surface. The device also comprises a voltage generator, capable of supplying an increasing voltage between the electrodes, and a voltage meter capable of indicating the voltage between the electrodes. The voltage meter indicates the voltage between the electrodes when current between the electrodes reaches a predetermined value.

18 Claims, 3 Drawing Sheets

METHOD AND APPARATUS FOR MEASURING PROPERTIES OF A TARGET SURFACE

FIELD OF THE INVENTION

The invention relates to an apparatus and method using electrical current to measure certain properties of a target surface having a substrate with an insulative coating thereon, and is particularly useful for measuring properties of naturally occurring tissue, and more particularly for measuring properties of the stratum corneum.

BACKGROUND OF THE INVENTION

For years those of ordinary skill in the art have attempted to make measurements of various properties of target surfaces. As used herein, a target surface comprises a substrate having one or more aesthetically, electrically or otherwise functionally distinguishable layers superimposed thereon. The substrate may be disposed between other components of system under consideration or may be the inner component of the system under consideration. At least one superimposed layer is disposed on the substrate and may provide a protective function or other functionality. The protective layer under consideration is the outwardly facing protective layer, which is exposed when the target surface is in use. To be distinguishable and measurable according to the present invention, it is only necessary that the superimposed layer of the target surface have a greater electrical resistance than the substrate and is relatively thin, as discussed below.

The measurements of the present invention are applicable to target surfaces comprising natural tissue. As used herein, natural tissue comprises tissue originating from the animal, plant and mineral kingdoms.

A target surface of particular interest is the human skin. The measurement of various properties of the human skin is important, as the stratum corneum, i.e. the outermost layer of the human skin, provides several functions. For example, the stratum corneum provides a barrier between the inside of the body and the outside world. Maintaining this barrier is important to preventing the intrusion of chemicals, bacteria and viruses into the body. The stratum corneum also regulates the evacuation of moisture from the body. However, measurement of the barrier properties of the human skin must be sanitary, noninvasive and usable with people of differing ages and health conditions.

The barrier properties of the skin are typically measured by transepidermal water loss. However, this measurement relies upon complex equipment and can be influenced by unrelated health and environmental factors, such as humidity, alcohol intake, Parkinson's disease and certain headaches. Transepidermal water loss is discussed in more detail in Chap. 9 of the Handbook of Non-invasive Methods and the Skin, editors Serup and Jemec, published by CRC Press, copyright 1995, incorporated herein by reference.

Likewise, other target surfaces of interest include the skin of pets, such as dogs and cats. The condition of the pet's skin can indicate the general overall health and nutrition of the pet. This feature is particularly important, as the pet cannot directly communicate its health concerns or needs.

U.S. Pat. No. 5,738,107 iss. Apr. 14, 1998 to Martinsen et al., discloses a technique for measuring the moisture content of the skin by placing three electrodes in contact with the skin. A voltage having a frequency less than 50 kHz is applied to the electrodes. The susceptance is then measured under the electrodes. Yet other attempts in the art directly measure phase angle. Illustrative are U.S. Pat. No. 3,665,302 iss. May 23, 1972 to Lees et al.; U.S. Pat. No. 4,758,778 iss. Jul. 19, 1988 to Kristinsson; and GB 22988923 pub. Sep. 18, 1996. However, each of these attempts relies upon AC and complex measurements of phase angle.

U.S. Pat. No. 6,085,115 iss. Jul. 4, 2000 to Weaver et al, discloses a a biopotential measurement that decreases the resistance of the skin to electrical fields. The topical application of a resistance-decreasing agent is also taught in order to diminish unwanted voltages, which compete with the biopotential measurements. The biopotential measurement is made at a skin surface site, which is electroporated through strong electric field pulses. In this method, electroporation is used as an auxiliary means to improve quality of the biopotential measurements and does not indicate properties of the skin.

WO 001301 A1, published Jul. 6, 1999 to Szopinski teaches measurement of skin resistance/impedance. Both alternating and direct current may be used to yield AC impedance or DC resistance, respectively. However, each of these teachings relies upon a resistance/impedance measurement to determine skin properties. Resistance measurements are dependent on the value of applied voltage and a number of other factors and, hence, may have low accuracy. Impedance measurement methods have better accuracy but they require complex equipment due to high frequencies involved.

U.S. Pat. No. 5,239,258 iss. Aug. 24, 1993 to Kauffman teaches a method of measuring the freshness of fuels, oils, and food products by, inter alia, dissolving a sample of the material to be tested in a solvent. The solvent is selected to dissolve both the material and its oxidation products. This procedure is infeasible when one wishes to preserve the integrity of the sample.

None of the attempts in the prior art known to the inventor teach a method of measuring properties of the skin utilizing relatively high voltages and which rely upon or cause ion transfer through the stratum corneum.

Furthermore, the method and apparatus of the present invention may be broadly applied to measurements of the barrier properties of many natural coatings disposed on many natural substrates, particularly those that are electrically conductive. For example, the present invention may be used to measure certain properties of any thin insulating layer deposited on the surface of a conductive natural substrate, e.g. the permeability of the waxy layer of a plant leaf, barrier properties of a plant root, the effectiveness of chemical coatings on plants, the grade of leather, waterproof resistance of cloth, residual dust/dirt on conductive surfaces, bacteriological, viral, mold or other contamination on conductive surfaces. For example, the invention may be used to test food products, e.g. as the outer layers of vegetables such as potatoes, carrots, apples and oranges.

SUMMARY OF THE INVENTION

In one embodiment the invention comprises a method for measuring the barrier properties of a target surface comprising natural tissue. The method comprises the steps of providing a probe. The probe has a pair of spaced apart electrodes in electrical communication with each other, providing a voltage generator, capable of supplying an increasing voltage between said electrodes, and providing a voltage meter capable of indicating the voltage between said electrodes. The electrodes are placed in contact with the skin of a test subject. An increasing voltage is supplied from the voltage generator to the electrodes until current between said electrodes reaches a predetermined value. The voltage, which occurs when said current reaches the predetermined value, is noted.

In another embodiment the invention comprises a device for measuring the barrier properties of a target surface comprising natural tissue. The device comprises a probe. The probe has a pair of spaced apart electrodes in electrical communication with each other. The electrodes are contactable with the skin of a subject. The device also comprises a voltage generator, capable of supplying an increasing voltage between the electrodes, and a voltage meter capable of indicating the voltage between the electrodes. The voltage meter indicates the voltage between said electrodes when current therebetween reaches a predetermined value.

One of skill will recognize the aforementioned method and device have applicability to measurements of the target surface moisture content, barrier properties and other properties as well. For example, measurements of other barriers, coatings, and laminae on various substrates may be made according to the present invention.

DETAILED DESCRIPTION OF THE INVENTION

Figure 1:
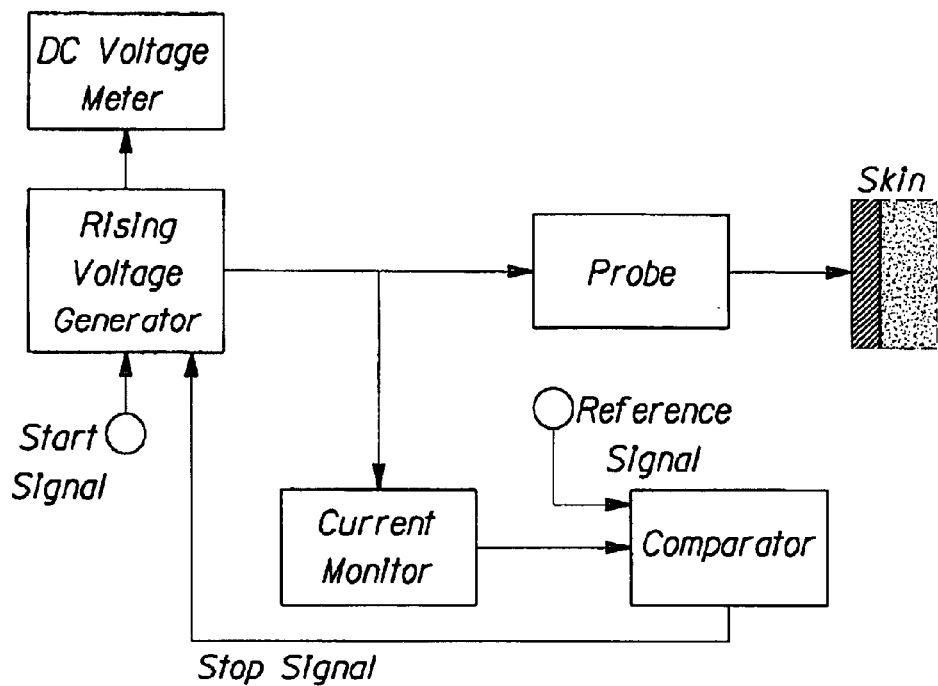
FIG. 1 is a schematic electrical diagram of a device according to the present invention.

Referring to FIG. 1, in one embodiment the invention comprises a device for measuring barrier properties of the skin or other protective layers of a target surface. The device comprises a probe 10 having two electrodes 12 for contacting the surface to be measured, a voltage generator for supplying a an electric potential to the probe 10, a voltage meter indicating the voltage supplied to the probe 10, and a current meter indicating the current between the electrodes 12.

The apparatus and method of the present invention are noninvasive. By noninvasive it is meant that the device does not penetrate or cause damage to the target surface. The apparatus and method also do not measure the electrical resistance of the target surface as occurs with many teachings of the prior art. Likewise, a phase shift, as may occur with alternating current is not measured according to the present invention. Instead, the present invention measures a nonlinear response to an applied voltage.

The apparatus according to the present invention may be placed in fixed location. In one embodiment the apparatus is portable and can be used in a variety of positions and orientations.

Figure 2:
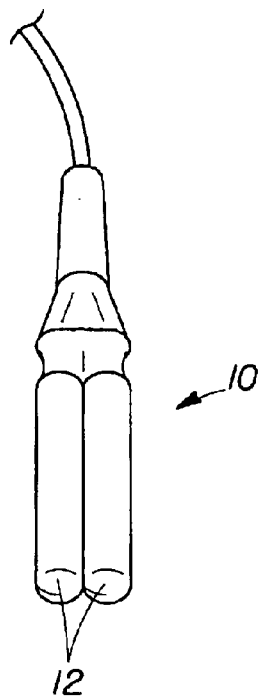
FIG. 2 is a perspective view of an exemplary probe according to the present invention.

Referring to FIG. 2 and examining the device in more detail, the probe 10 has first and second electrodes 12. Each electrode 12 is contactable with the target surface. Each electrode 12 has a proximal end proximate the voltage generator, and a distal end for contacting the target surface. Preferably the distal end of the electrode 12 has a contact area large enough to prevent damage to the target surface and discomfort to the subject if the device testing a human or animal.

The amount of contact area is dependent upon the pressure to be applied by the electrode 12. For the embodiments described herein, the electrodes 12 may apply a contact pressure of 10 to 100 grams per square meter. To ensure precision in the measurement, a contact pressure of 50 grams per square meter may be utilized. If desired, the electrodes 12 or the entire probe 10 may be spring loaded to provide the desired contact pressure. For the embodiments described herein, the distal ends of the electrodes 12 may have a contact area of 0.5 to 10 square millimeters. To ensure precision in the measurement a contact area of 2 square millimeters may be utilized.

Preferably the distal end of the electrode 12 is round in cross section. The distal end of the electrode 12 may be ground to a highly polished surface finish to ensure proper electrical contact with the target surface. The electrodes 12 may have a convex shape at the distal end. If a convex shape is chosen for the electrodes 12, they may be spherical, having a radius of curvature of 0.05 to 5 millimeters and more particularly 2 millimeters.

The electrodes 12 may be thought of as two points separated by a variable or predetermined distance. The spacing between the electrodes 12 should be greater than the thickness of the layer of the target surface, in order to ensure the desired electrical path occurs. The desired electrical path according to the present invention is from one electrode 12, through the layer, into the substrate, back through the layer and into the other electrode 12. If the electrodes 12 are spaced too close together, the electrical path may be shunted therebetween, without reaching the substrate. For the embodiments described and claimed herein, when the electrodes 12 contact the target surface they may be spaced apart a distance less than that needed to achieve a significant voltage drop in the target substrate. The electrodes 12 may be spaced apart on a pitch of 2 to 8 millimeters in a first embodiment and 5 millimeters in a second embodiment.

Figure 3:
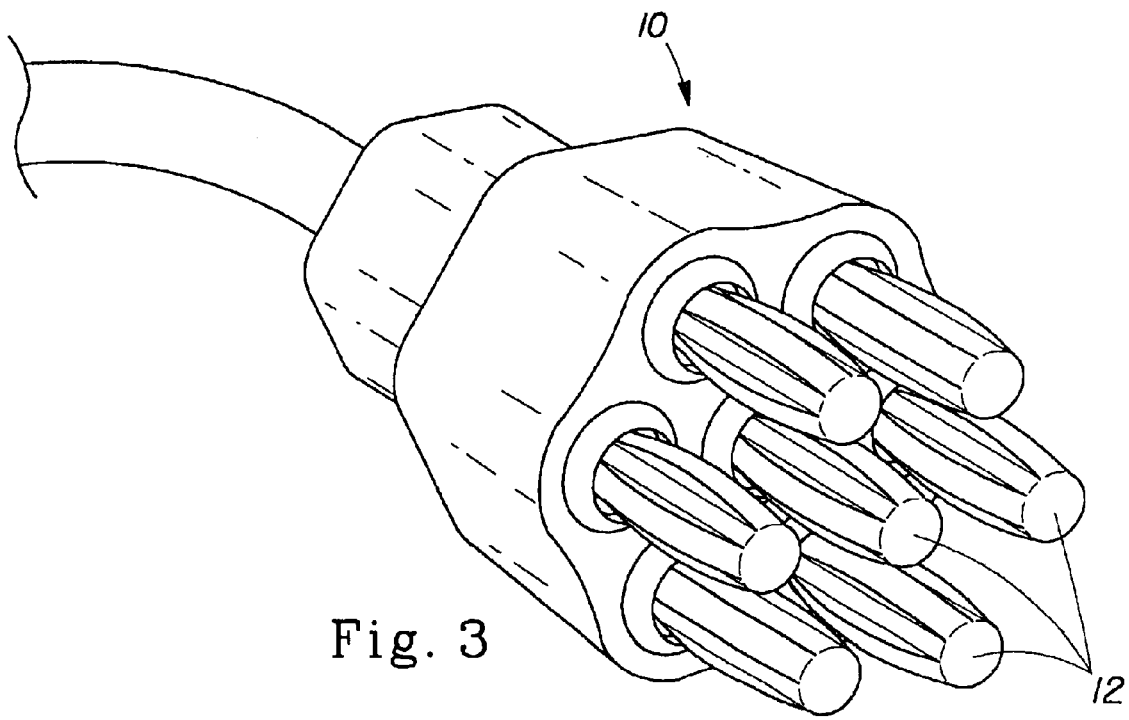
FIG. 3 is a perspective view of an alternative embodiment of a probe according to the present invention and having a first electrode with a plurality of discrete contact surfaces circumferentially disposed around a second electrode.

Referring to FIG. 3, the first electrode 12 may comprise a plurality of discrete contact surfaces. The plural contact surfaces of the first electrode 12 may be equally or unequally spaced from the second electrode 12. In one suitable embodiment, the contact surfaces of the first electrode 12 are disposed around the second electrode 12 in a circular geometry. In this geometry, the contact surfaces may be equally radially spaced from the second electrode 12 and equally circumferentially spaced from each other. Alternatively, the contact surfaces may be equally radially spaced from the second electrode 12 and unequally circumferentially spaced from each other, if there is concern that the target surface is not axi-resistant to electric current flow therethrough. Either the first electrode 12 or second electrode 12 may be the anode/cathode.

In yet another alternative embodiment, the second electrode 12 may completely circumscribe the first, separated by an equal or unequal annular clearance. In yet another embodiment, the second electrode 12 may be interposed between two contact surfaces of the first electrode 12, one contact surface circumbscribing the second electrode 12, which, in turn, circumscribes the other contact surface of the first electrode 12. The embodiments having electrodes 12, or contact surfaces thereof, circumscribing other electrodes 12, may utilize either concentric or eccentric geometries.

Referring back to FIG. 1, the device also comprises a voltage generator. The voltage generator may provide direct current, although alternating current is also contemplated. Direct current provides the advantage that no capacitance effects will be encountered, as is known to one of skill.

Figure 4A:
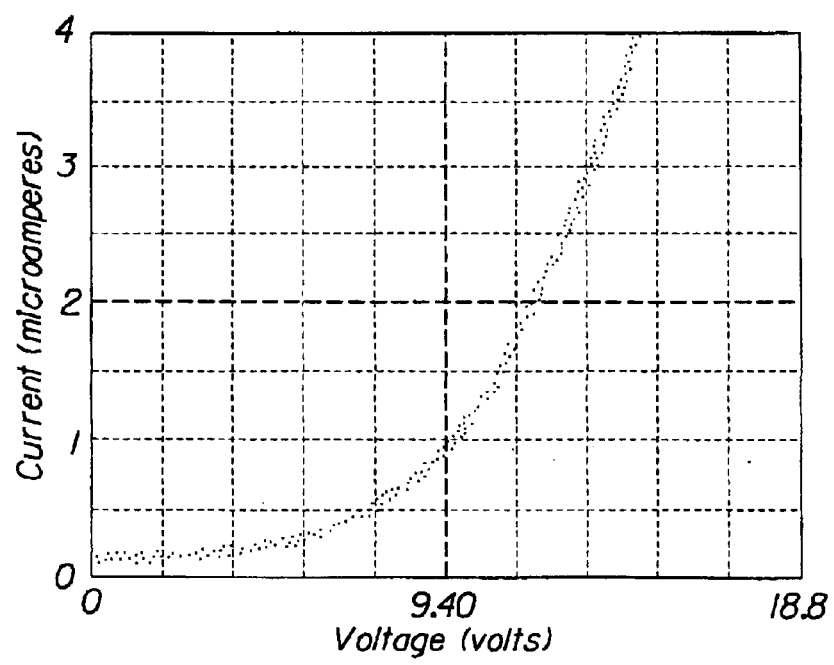
FIGS. 4A, 4B, and 4C are graphical representations of tests according to the present invention, measuring the barrier properties of the stratum corneum of human skin on a 42 year old Caucasian male wherein FIG. 4A was measured on the right cheek, FIG. 4B was measured on the left cheekbone and FIG. 4C was measured on the left side of the forehead.
Figure 4B:
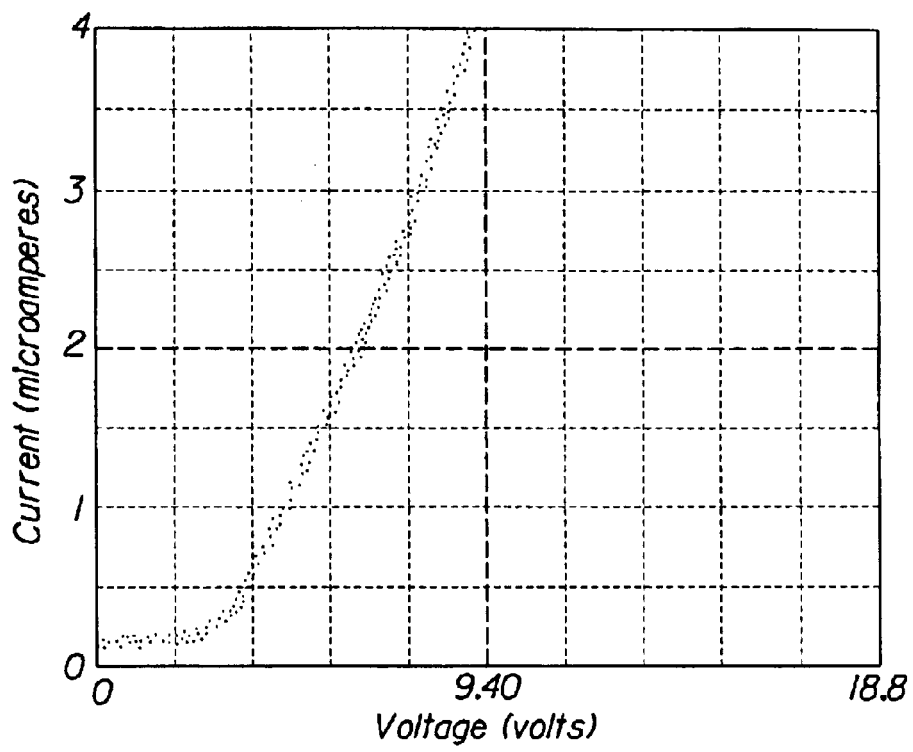
Figure 4C:
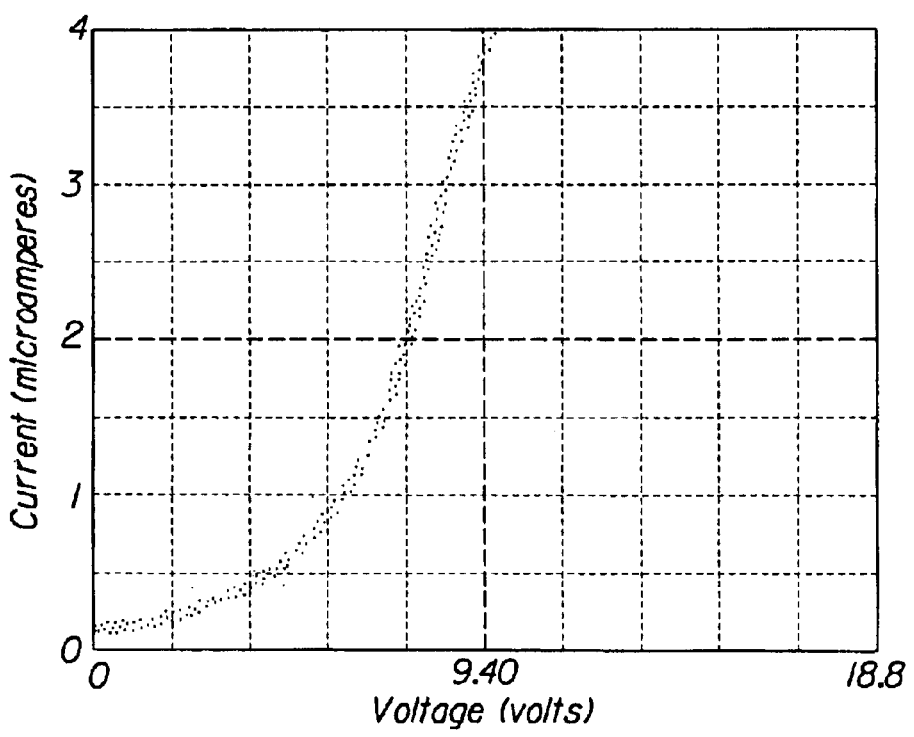

Referring to FIGS. 4A, 4B and 4C the voltage generator may provide a voltage increasable from a baseline value to a threshold value. The baseline value is the initial value of the voltage at the time the electrodes 12 contact the target surface. The threshold value is the value of the voltage at the time during the test that the current between the electrodes 12 reaches a predetermined value. Typically the value of the threshold voltage will be greater than the value of the baseline voltage. The voltage may be increasable from 0 to 200 volts in a first embodiment, and from 0 to 30 volts in a second embodiment. The voltage may be monotonically increased from 0 volts to the maximum voltage applied during a particular test.

The measurements of FIGS. 4A–4C were carried out with a monotonically increasing voltage rate of 1.5 volts per second, using probes 10 contact pressure of 50 grams per square meter, spherically shaped distal ends having a diameter of 5 millimeters, and electrodes 12 spaced apart on a pitch of 8 millimeters. For illustrative purposes, the measurements of FIGS. 4A–4C were not terminated when the threshold current was reached. The threshold current and associated voltage for the measurements illustrated in each of FIGS. 4A–4C are shown in Table 1 below:

TABLE 1

| FIG. | Threshold current (microamperes) | Applied voltage at Threshold Current (volts) |
| --- | --- | --- |
| 4A | 1 | 10.2 |
| 4B | 1 | 4.7 |
| 4C | 1 | 6.6 |

The predetermined current may be from 0.1 to 5 microamperes, and specifically 1 microampere. If the predetermined current is too high, it may damage or cause pain to the target surface. If the predetermined current is too low, background noise may interfere with the accuracy of the measurement, unless special instrumentation is used.

If the voltage is monotonically increased, it may be increased at a rate of 0.1 to 10 volts per second. In one suitable embodiment, the voltage may monotonically increase at a rate of 1.5 volts per second. The voltage may be increased at a rate, which is less than the rate of the electrical response of the surface being tested. The rate of the electrical response of the subject is the rate of change of electric current through the subject upon application of a certain voltage applied as a step function. If desired, the voltage may be increased in a nonlinear fashion. For example, the applied voltage may increase very rapidly at the beginning of the test, then increase more slowly as the threshold value is approached. This procedure provides the advantage that total test time may be reduced, while allowing for accuracy around the threshold voltage.

Alternatively, the voltage may be increased from a baseline value to an upper value. The upper value may be greater than the threshold value of the voltage. When the upper voltage is reached, the voltage is reduced to a lower value, which is equal to or greater than the baseline voltage. The voltage is then in creased to a new upper voltage, which may be greater than the previous upper voltage. The voltage is then reduced until a new lower voltage, greater than the previous lower intermediate voltage is reached. This process is carried out for one or more cycles, until the threshold value is reached at least once. This procedure of nonmonotonically increasing the voltage may cause hysteresis in the current between the two electrodes 12. The hysteresis may provide further information about the target surface. For example, hysteresis may indicate the incipience, duration or relaxation time of aqueous pathways in the stratum corneum, as discussed below.

Referring back to FIGS. 1–2, a suitable voltage generator is commercially available from the Agilent Technologies, Inc of Palo Alto, Calif. under model number 33120A. Also, the invention comprises a current meter and voltage meter, each of suitable resolution and response time. A suitable combination meter is commercially available from Agilent Technologies, Inc. under model number 34401A.

If desired, the device may further comprise a reference signal generator and a signal comparator. The signal comparator compares the value of the current between the probes 10 to the value of the current of the reference signal. When the current between the electrodes 12 reaches a predetermined value, a stop signal is sent to the voltage generator. The voltage applied to the electrodes 12 does not further increase. This stop signal thus provides a safety feature for the device. When the stop signal is high, further increases in voltage and/or current to the electrodes 12 do not occur, preventing injury to the target surface. The stop signal may be activated when the current applied to the electrodes 12 reaches the value of the current of the reference signal. The current applied to the electrodes 12 may be indicated by the current meter.

The voltage, which occurs when the predetermined current is reached, is noted. If desired, this voltage may be recorded for future reference.

Without being bound by theory, it is believed that as the voltage is applied to human and other animal skin, the electric field creates aqueous pathways through the stratum corneum when the voltage reaches a certain level. The aqueous pathways allow ions from the epidermis to penetrate the stratum corneum. Ions travel through the aqueous pathways between the electrodes 12 and the epidermis. The ions create an electric current. This current increases with the applied voltage. The threshold voltage at which the predetermined current is reached is noted upon the predetermined current being reached. This voltage is directly proportional to the stratum corneum barrier capability, and inversely proportional to the moisture level in the SC. This process does not damage the skin or other target surface. Prophetically, the present invention can be utilized to measure the thickness and strength of paint/wax/stain or varnish on a metal substrate (for instance, a car body panel), the caliper of thin synthetic films, e.g. polyolefinics, and synthetic nonwovens, placed on a conductive substrate, etc.

What is claimed is:

1. A method for measuring properties of a target surface comprising natural tissue, said method comprising the steps of:

providing a probe, said probe having a pair of spaced apart electrodes in electrical communication with each other, providing a voltage generator, said voltage generator being capable of supplying an increasing voltage between said electrodes, providing a voltage meter, said voltage meter being capable of indicating the voltage between said electrodes, placing said electrodes in contact with the target surface, supplying a monotonically increasing voltage from said voltage generator to said electrodes until current between said electrodes reaches a predetermined value, and noting said voltage which occurs when said current reaches said predetermined value.

2. The method according to claim 1 wherein said predetermined current is from 0.1 to 3 microamperes.

3. The method according to claim 1 wherein said predetermined current is 1 microamperes.

4. The method according to claim 1 wherein said voltage increases at a rate of 0.1 to 10 volts per second.

5. The method according to claim 4 wherein said current nonlinearly increases from a baseline value to said predetermined value.

6. The method according to claim 4 wherein said current monotonically increases from a baseline value to said predetermined value.

7. The method according to claim 6 wherein said baseline value is 0 volts.

8. The method according to claim 1 wherein said target surface comprises animal tissue.

9. The method according to claim 8 wherein said target surface comprises human tissue.

10. A method for measuring properties of a target surface comprising natural tissue, said method comprising the steps of:

providing a probe, said probe having a pair of spaced apart electrodes in electrical communication with each other, providing a voltage generator, said voltage generator being capable of supplying an increasing voltage between said electrodes, providing a voltage meter, said voltage meter being capable of indicating the voltage between said electrodes, placing said electrodes in contact with the target surface, supplying an increasing voltage from said voltage generator to said electrodes until current between said electrodes reaches a predetermined value, and noting said voltage which occurs when said current reaches said predetermined value, said method further comprising the step of monitoring the current between said electrodes in real time.

11. A device for measuring the barrier properties of a target surface comprising natural tissue, said device comprising:

a probe, said probe having a pair of spaced apart electrodes in electrical communication with each other, said electrodes being spaced apart a distance of 3 to 10 mm, said electrodes being contactable with the skin of a subject, a voltage generator, said voltage generator being capable of supplying an increasing voltage between said electrodes, a voltage meter, said voltage meter being capable of indicating the voltage between said electrodes, whereby said voltage meter indicates the voltage between said electrodes when current therebetween reaches a predetermined value.

12. A device according to claim 11 wherein each said electrode has a contact area of at least 0.01 square mm.

13. A device according to claim 12 wherein at least one said electrode has a contact area of at least 1 square mm.

14. A device according to claim 11 having a first electrode and a second electrode, wherein said first electrode comprises a plurality discrete contact surfaces, said plurality of discrete contact surfaces being disposed about said second electrode in a radial pattern.

15. A device according to claim 14 wherein said first electrode circumscribes said second electrode.

16. A device according to claim 11 wherein said voltage generator provides a voltage increasable from 0 to 30 volts.

17. A device according to claim 16 wherein said voltage is monotonically increasable at a rate of 0.1 to 10 volts per second.

18. A device according to claim 11 comprising a DC voltage generator.

* * * * *